United States Patent
Kuroki et al.

(10) Patent No.: US 9,566,036 B2
(45) Date of Patent: Feb. 14, 2017

(54) MEDICAL DOSE INFORMATION MANAGEMENT APPARATUS, X-RAY DIAGNOSTIC APPARATUS, AND MEDICAL DOSE INFORMATION MANAGEMENT METHOD

(71) Applicant: TOSHIBA MEDICAL SYSTEMS CORPORATION, Otawara-Shi (JP)

(72) Inventors: Takahiro Kuroki, Nasushiobara (JP); Naobumi Ishikawa, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 260 days.

(21) Appl. No.: 14/446,646

(22) Filed: Jul. 30, 2014

(65) Prior Publication Data
US 2015/0036803 A1    Feb. 5, 2015

(51) Int. Cl.
A61B 6/00    (2006.01)

(52) U.S. Cl.
CPC .............. *A61B 6/463* (2013.01); *A61B 6/487* (2013.01); *A61B 6/5294* (2013.01); *A61B 6/461* (2013.01); *A61B 6/542* (2013.01)

(58) Field of Classification Search
CPC ......... A61B 6/461; A61B 6/463; A61B 6/487; A61B 6/5294; A61B 6/542
See application file for complete search history.

(56) References Cited

U.S. PATENT DOCUMENTS

| | | | |
|---|---|---|---|
| 7,974,714 B2 | 7/2011 | Hoffberg | |
| 2005/0152493 A1* | 7/2005 | Seto | A61B 6/032 378/20 |
| 2010/0239069 A1* | 9/2010 | Bourdeaux | A61B 6/00 378/96 |

FOREIGN PATENT DOCUMENTS

| | | |
|---|---|---|
| JP | 6-47031 | 2/1994 |
| JP | 2007-181737 | 7/2007 |
| JP | 4612319 | 1/2011 |

* cited by examiner

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

A medical dose information management apparatus according to an embodiment includes a dose measuring unit, a dose graph generation unit, a dose graph generation unit, a display mode setting unit and an output unit. The dose measuring unit acquires dose information including an area dose in X-ray irradiation. The dose graph generation unit generates, based on the dose information, a dose graph indicating area doses respectively corresponding to imaging operations associated with the X-ray irradiation. The display mode setting unit sets a display mode for the dose graph in accordance with each of imaging schemes corresponding to the imaging operations included in the dose information. The output unit outputs the dose graph accompanied by the set display mode.

17 Claims, 12 Drawing Sheets

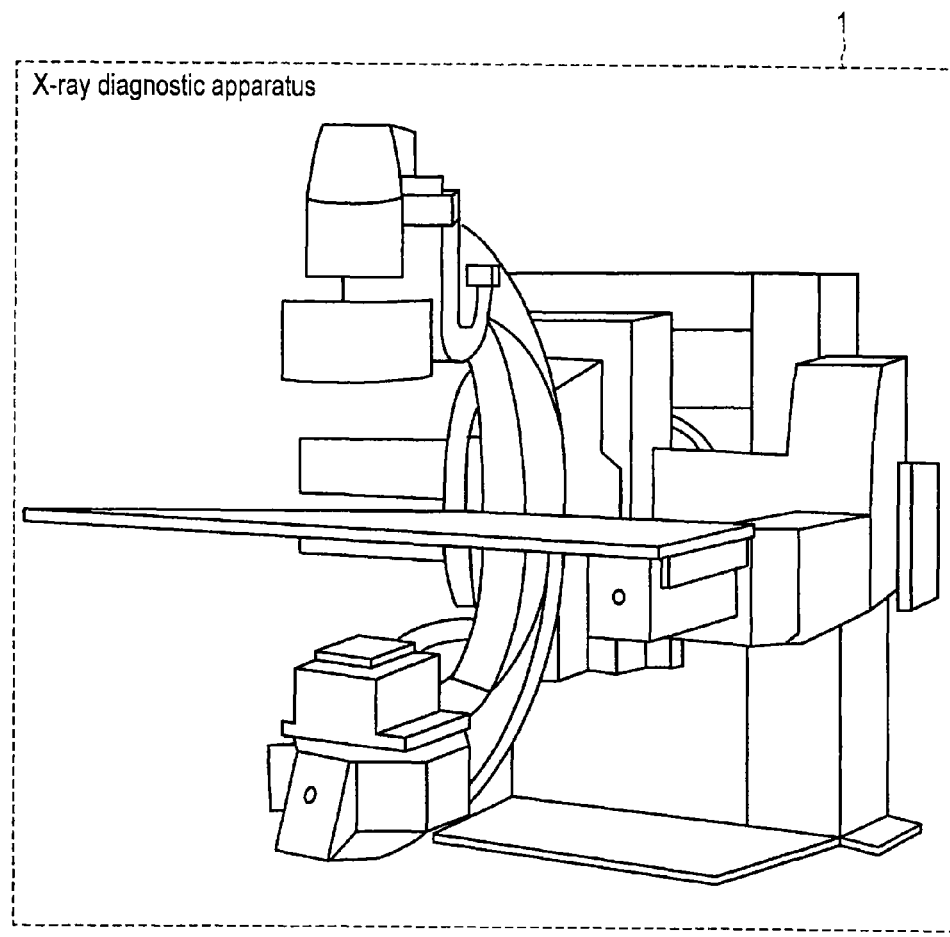
F I G. 3

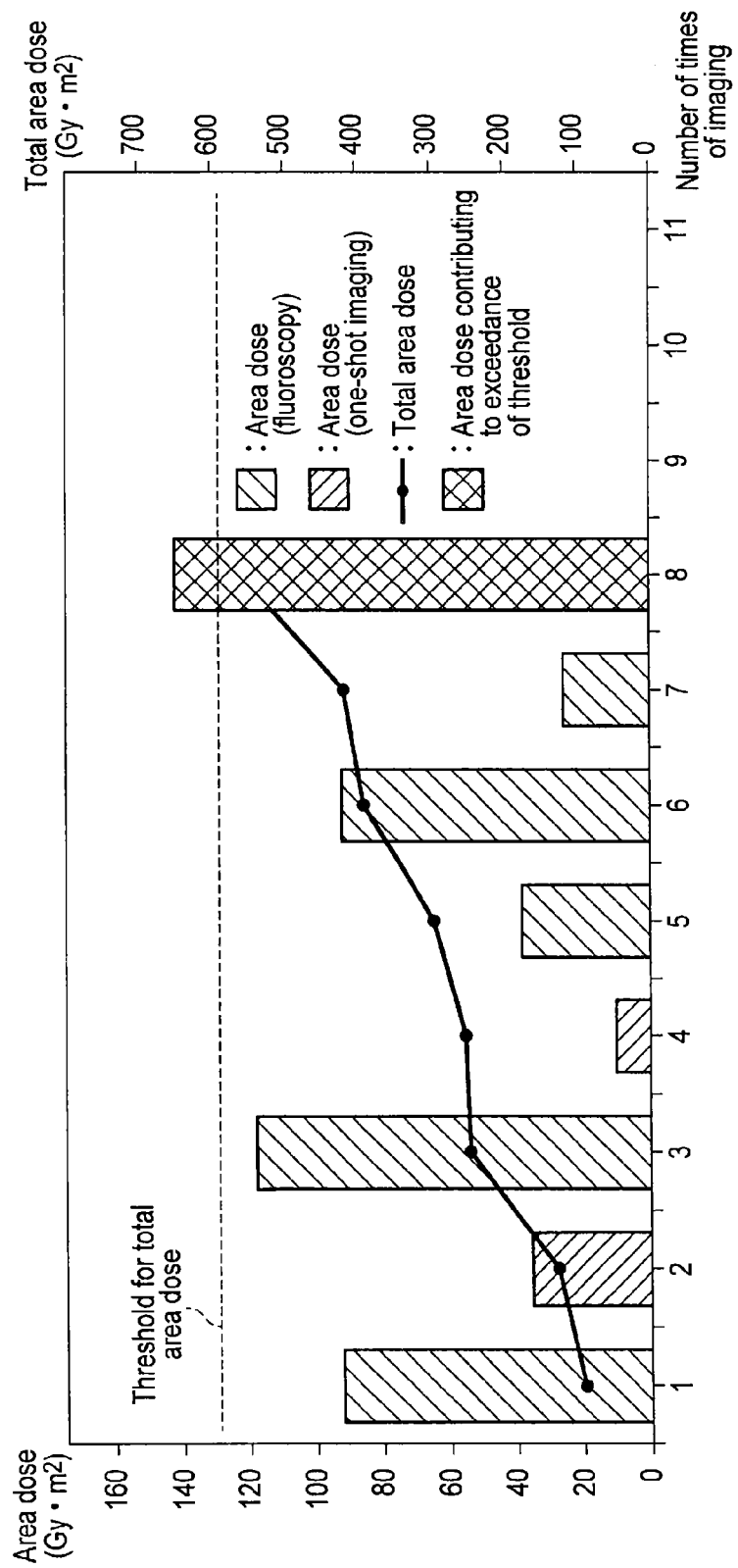
F I G. 8

MEDICAL DOSE INFORMATION MANAGEMENT APPARATUS, X-RAY DIAGNOSTIC APPARATUS, AND MEDICAL DOSE INFORMATION MANAGEMENT METHOD

REFERENCE TO RELATED APPLICATIONS

This application is based upon and claims the benefit of priority from the prior Japanese Patent Application No. 2013-157978, filed Jul. 30, 2013, the entire contents of which are incorporated herein by reference.

FIELD

Embodiments described herein relate generally to a medical dose information management apparatus, an X-ray diagnostic apparatus, and a medical dose information management method.

BACKGROUND

Conventionally, in X-ray imaging using an X-ray diagnostic apparatus, exposure information (dose information) of an object is stored as additional information together with an acquired image. Acquired images and exposure doses accompanying the acquired images are often managed upon being linked to each other. In addition, acquired images and exposure doses accompanying the acquired images are sometimes sent to an external server or the like. At this time, the server manages dose information concerning each object.

However, dose information is handled as additional information of an acquired image, and hence is not effectively used for exposure management for an object during an examination. For example, in an X-ray examination of an object, it is difficult for the operator to grasp a change in exposure dose for an object accompanying a plurality of X-ray imaging operations. It is also difficult for the operator to grasp a reference for a radiation dose permitted for an object with respect to a predetermined value of a total exposure dose.

BRIEF DESCRIPTION OF THE DRAWINGS

FIG. 3 is a perspective view showing an example of the outer appearance of the X-ray diagnostic apparatus according to this embodiment;

FIG. 8 is a view showing a predetermined threshold together with a dose graph according to the third modification of this embodiment;

DETAILED DESCRIPTION

Figure 1:
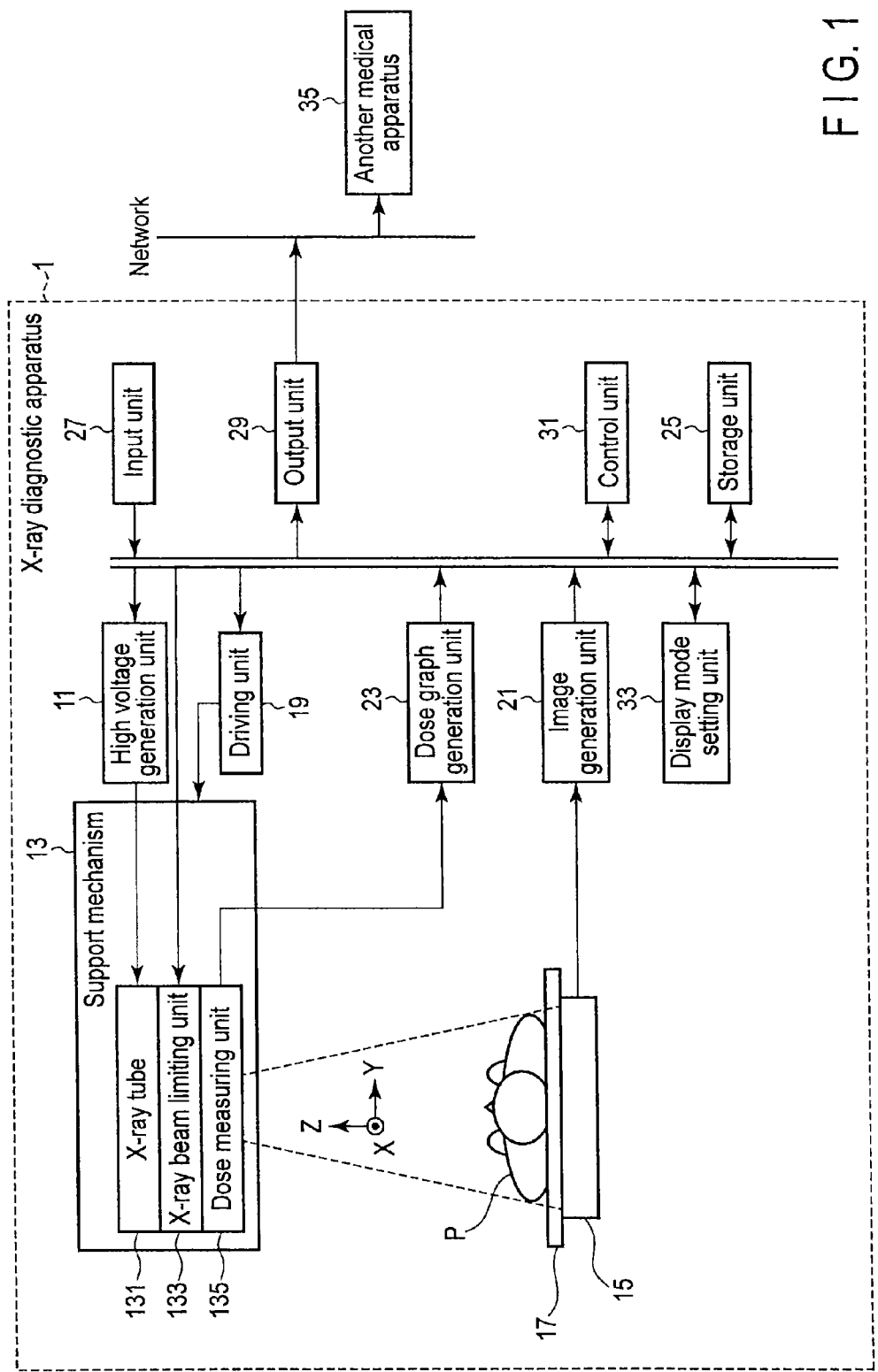
FIG. 1 is a block diagram showing an example of the arrangement of an X-ray diagnostic apparatus according to an embodiment.

In general, according to one embodiment, a medical dose information management apparatus includes a dose measuring unit, a dose graph generation unit, a dose graph generation unit, a display mode setting unit and an output unit. The dose measuring unit acquires dose information including an area dose in X-ray irradiation. The dose graph generation unit generates, based on the dose information, a dose graph indicating area doses respectively corresponding to imaging operations associated with the X-ray irradiation. The display mode setting unit sets a display mode for the dose graph in accordance with each of imaging schemes corresponding to the imaging operations included in the dose information. The output unit outputs the dose graph accompanied by the set display mode.

An X-ray diagnostic apparatus according to an embodiment will be described below with reference to the accompanying drawing. Note that the same reference numerals in the following description denote constituent elements having almost the same functions and arrangements, and a repetitive description will be made only when required.

FIG. 1 shows the arrangement of an X-ray diagnostic apparatus 1 according to the first embodiment. The X-ray diagnostic apparatus 1 includes a high voltage generation unit 11, a support mechanism 13 which supports an X-ray tube 131, an X-ray beam limiting unit 133, and a dose measuring unit 135, an X-ray detector 15 which detects X-rays, a bed (not shown) including a top 17 on which an object P is placed, a driving unit 19 which drives the support mechanism 13, an image generation unit 21, an interface unit (not shown), a dose graph generation unit 23, a storage unit 25, an input unit 27, an output unit (display unit) 29, a control unit 31, and a display mode setting unit 33.

Figure 2:
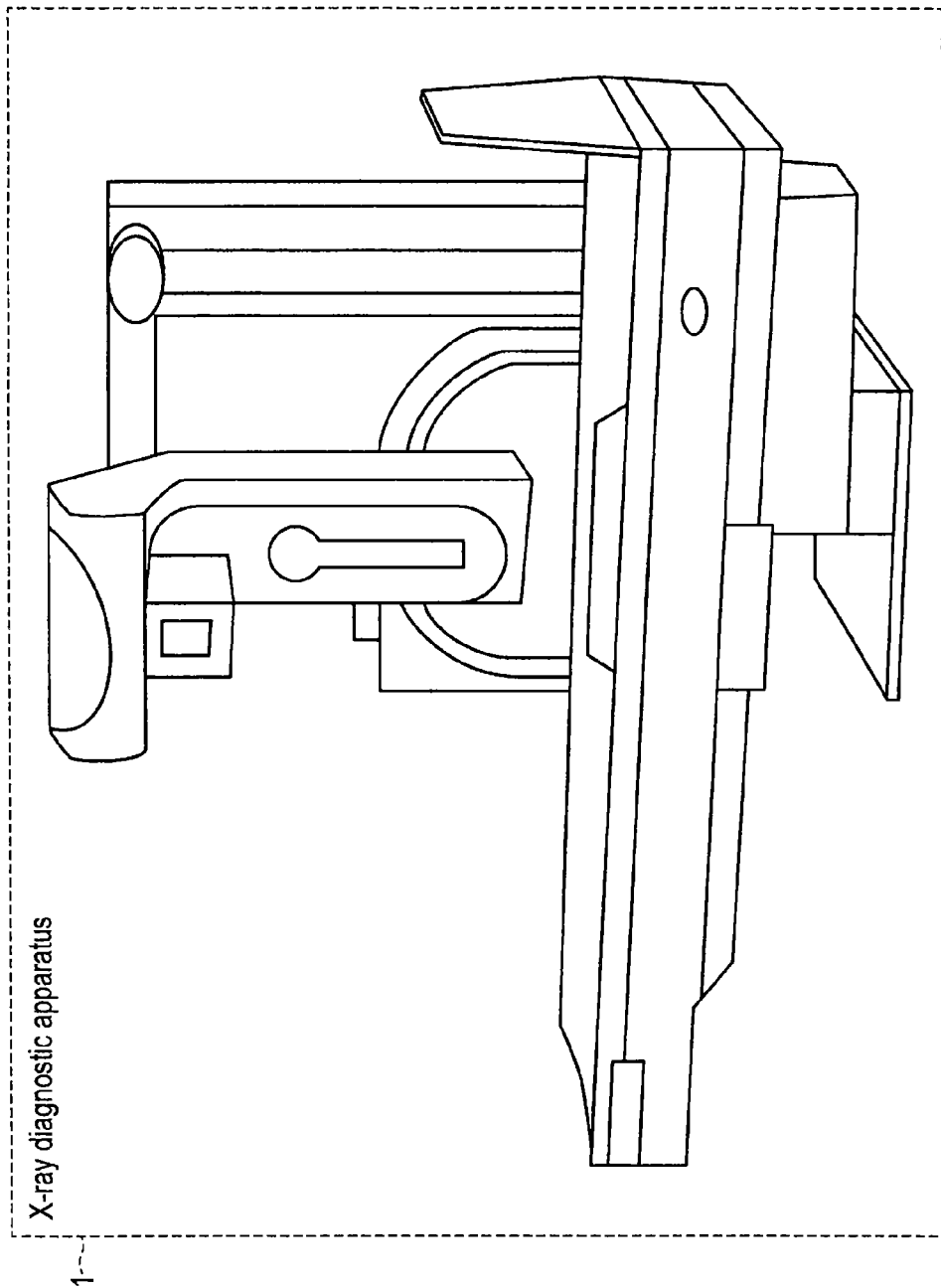
FIG. 2 is a perspective view showing an example of the outer appearance of the X-ray diagnostic apparatus according to this embodiment.

FIGS. 2 and 3 are views showing an example of the outer appearance of the X-ray diagnostic apparatus 1 according to this embodiment. The X-ray diagnostic apparatus 1 shown in FIGS. 2 and 3 is, for example, an X-ray TV system. Note that the X-ray diagnostic apparatus 1 according to the embodiment is not limited to an X-ray TV system. For example, the embodiment can be applied to an arbitrary X-ray diagnostic apparatus such as a general X-ray imaging system, X-ray angiographic system, mobile X-ray diagnostic apparatus, or portable X-ray diagnostic apparatus.

The high voltage generation unit 11 generates a tube current to be supplied to the X-ray tube 131 and a tube voltage to be applied to the X-ray tube 131 in accordance with each of a plurality of X-ray irradiation operations. A plurality of X-ray irradiation operations are, for example, a plurality of one-shot imaging operations and a plurality of fluoroscopic operations. One-shot imaging is to image an object P by irradiating it with X-rays once. Fluoroscopy is to image the object P by intermittently irradiating it with X-rays a plurality of times in accordance with a preset pulse width and exposure time. An imaging period concerning fluoroscopy will be referred to as an irradiation period hereinafter. For example, one-shot imaging and fluoroscopy correspond to imaging types. Note that imaging types are not limited to one-shot imaging and fluoroscopy and include arbitrary imaging methods.

More specifically, the high voltage generation unit 11 supplies tube currents suitable for one-shot imaging and fluoroscopy to the X-ray tube 131, and applies tube voltages suitable for one-shot imaging and fluoroscopy to the X-ray tube 131 under the control of the control unit 31 in accordance with X-ray conditions. For example, the high voltage generation unit 11 applies a tube voltage to the X-ray tube 131 and supplies a tube current to the X-ray tube 131 a plurality of times in fluoroscopy of the object P.

X-ray conditions include, for example, a tube voltage, a tube current, and a tube current-time product obtained by multiplying the tube current by an exposure time. Note that X-ray conditions may include the distance (to be referred to as SID (Source Image Distance) hereinafter) between the focal point (to be referred to as a tube focal point hereinafter) of X-ray generation by the X-ray tube 131 and the X-ray detector 15 and an X-ray irradiation range (to be referred to as an irradiation area hereinafter) at a predetermined reference position. The predetermined reference position is, for example, a position 15 cm immediately above the top 17. X-ray conditions correspond to various types of conditions concerning the above X-ray irradiation.

The support mechanism 13 supports the X-ray tube 131, the X-ray beam limiting unit 133, the dose measuring unit 135, and the like so as to make them movable along three orthogonal axes (to be described later). More specifically, the support mechanism 13 supports the X-ray tube 131, the X-ray beam limiting unit 133, the dose measuring unit 135, and the like so as to make it possible to change the SID.

Note that the support mechanism 13 may include, for example, a C-arm and a C-arm support portion. The X-ray tube 131 and the X-ray detector 15 are mounted on C-arm so as to face each other. Note that an Ω-arm may be used in place of the C-arm. The C-arm support portion supports the C-arm so as to make it slidable in a direction (to be referred to as the first direction hereinafter) along the C-shape. The C-arm support portion supports the C-arm so as to make it rotatable almost about a connecting portion which connects the C-arm to the C-arm support portion in a direction (to be referred to as the second direction hereinafter) perpendicular to the first direction. Note that the C-arm support portion can support the C-arm so as to make it translatable in the short-axis direction and long-axis direction of the top 17.

The X-ray tube 131 generates X-rays at a tube focal point based on the tube current supplied from the high voltage generation unit 11 and the tube voltage applied from the high voltage generation unit 11. The X-rays generated from the tube focal point are applied to the object P through the X-ray irradiation window provided in the front surface of the X-ray tube 131.

The X-ray beam limiting unit 133 is provided on the front surface of the X-ray irradiation window of the X-ray tube 131. That is, the X-ray beam limiting unit 133 is provided between the X-ray tube 131 and the X-ray detector 15. More specifically, the X-ray beam limiting unit 133 limits the irradiation range having the maximum aperture (to be referred to as the maximum irradiation range hereinafter) so as to prevent a portion other than the imaging region (X-ray irradiation region) desired by the operator from being unnecessarily exposed to the X-rays generated at the tube focal point in accordance with an irradiation area for irradiating the body surface of the object P with X-rays. For example, the X-ray beam limiting unit 133 limits an irradiation range by moving each of a plurality of aperture blades in accordance with the instruction to limit an irradiation range which is input from the input unit 27. That is, the X-ray beam limiting unit 133 stops down the X-rays generated by the X-ray tube 131 to irradiate a region (X-ray irradiation region) of the object, which is desired by the operator, with the X-rays.

More specifically, the X-ray beam limiting unit 133 includes a plurality of first aperture blades movable in a predetermined direction and a plurality of second aperture blades movable in a direction perpendicular to the predetermined direction. Each of the first and second aperture blades is formed from lead which shields X-rays generated at the tube focal point.

Note that the X-ray beam limiting unit 133 may include a plurality of filters (to be referred to as compensating filters hereinafter) which are inserted in the irradiation field of X-rays to reduce the exposure dose for the object P and improve image quality. The plurality of compensating filters respectively have different thicknesses. Note that the respective compensating filters have the same thickness, and may be formed from different materials. Each compensating filter changes the radiation quality of X-rays generated at the tube focal point in accordance with the thickness. Each compensating filter is formed from aluminum, copper, or the like. The operator selects the compensating filter via the input unit 27 in accordance with an imaging plan for the object P. The compensating filter selected from the plurality of compensating filters is inserted into the irradiation filed of X-rays at the X-ray beam limiting unit 133 under the control of the control unit 31.

Each compensating filter reduces low-energy X-ray components (soft X-ray components), of the X-rays generated at the tube focal point (to be referred to generated X-rays hereinafter), which are easily absorbed by the object P, to reduce the exposure of the object P to X-rays in order to prevent, for example, halation. Alternatively, each compensating filter may reduce high-energy X-ray components, of the generated X-rays, which cause a reduction in the contrast of the medical image generated by the image generation unit 21.

The dose measuring unit 135 acquires dose information containing a plurality of area doses respectively corresponding to a plurality of X-ray irradiation operations for the object P. The dose measuring unit 135 acquires an area dose based on, for example, an output from a dosimeter provided on the front surface of the X-ray irradiation window of the X-ray tube 131. That is, the dosimeter is provided between the X-ray beam limiting unit 133 and the X-ray detector 15. The dosimeter is, for example, an area dosimeter. The dosimeter measures an area dose throughout a predetermined period. The predetermined period corresponds to a readout period during which information is read out from the dosimeter (to be referred to as a dose readout period hereinafter). The dosimeter outputs the area dose read out for each dose readout period to the dose graph generation unit 23 and the storage unit 25.

The dose measuring unit 135 sequentially acquires dose information in accordance with imaging of an object. Dose information includes the area dose output from the dosimeter. For example, the dose measuring unit 135 sequentially acquires dose information from the dosimeter in accordance with a dose readout period in fluoroscopy. The dose measuring unit 135 outputs the acquired dose information to the dose graph generation unit 23.

The X-ray detector 15 detects the X-rays generated from the X-ray tube 131 and transmitted through the object P. The X-ray detector 15 is, for example, an FPD (Flat Panel Detector). The FPD 15 includes a plurality of semiconductor detection elements. Semiconductor detection elements include direct and indirect conversion type semiconductor detection elements. The direct conversion type is a type that directly converts incident X-rays into electrical signals. The indirect conversion type is a type that converts incident X-rays into light through a phosphor and converts the light into electrical signals.

The electrical signals generated by the plurality of semiconductor detection elements as X-rays strike them are output to an A/D converter (Analog to Digital converter). The A/D converter converts the electrical signals into digital data. The A/D converter outputs the digital data to a preprocessing unit (not shown). Note that as the X-ray detector 15, an image intensifier may be used.

A bed (not shown) includes the tabletop 17 on which the object P is placed. Note that the object P is placed on the tabletop 17. In addition, the X-ray detector 15 is provided below the tabletop 17.

The driving unit 19 drives the support mechanism 13 and the bed under the control of the control unit 31. More specifically, the driving unit 19 outputs a driving signal corresponding to a control signal from the control unit 31 to the support mechanism 13 to slide it in the first direction and rotate it in the second direction. At the time of fluoroscopy and one-shot imaging, the object P placed on the tabletop 17 is placed between the X-ray tube 131 and the X-ray detector 15. The driving unit 19 outputs the position of the X-ray tube 131 relative to the tabletop 17 and the position of the support mechanism 13 to the dose graph generation unit 23, the storage unit 25, and the like.

The driving unit 19 moves the top 17 by driving the top 17 under the control of the control unit 31. More specifically, the driving unit 19 slides the top 17 in the long-axis direction (the X direction in FIG. 1) of the top 17 and the short-axis direction (the Y direction in FIG. 1) of the top 17 based on control signals from the control unit 31. The driving unit 19 also moves the top 17 upward and downward in the vertical direction (the Z direction in FIG. 1). In addition, the driving unit 19 may rotate the top 17 to tilt it about at least one of the long-axis direction and the short-axis direction of the driving unit 19 as a rotation axis (the X-axis or the Y-axis in FIG. 1). The driving unit 19 outputs the position of the top 17 to the dose graph generation unit 23.

The driving unit 19 outputs the relative positional relationship between the X-ray tube 131 and the tabletop 17 to the dose graph generation unit 23. The relative positional relationship between the X-ray tube 131 and the tabletop 17 is, for example, the angle (tilt) of the X-ray tube 131 with respect to the tabletop 17. The tilt is represented by, for example, an Euler angle with reference to the isocenter relative to the object P.

The preprocessing unit (not shown) executes preprocessing for the digital data output from the X-ray detector 15. Preprocessing includes correction of sensitivity unevenness between the channels in the X-ray detector 15 and correction concerning an excessive decrease in signal level or data omission caused by an X-ray absorber such as a metal. The preprocessed digital data is output to the image generation unit 21.

The image generation unit 21 generates a acquired image based on preprocessed digital data after X-ray imaging at an imaging position of an object. The image generation unit 21 generates a fluoroscopic image based on preprocessed digital data after fluoroscopy at a fluoroscopy position. Acquired images and fluoroscopic images will be collectively referred to as projection images hereinafter. The image generation unit 21 associates a generated projection image with the dose graph generated by the dose graph generation unit 23 and outputs the resultant image to the output unit 29 and the storage unit 25.

An interface unit (not shown) is, for example, an interface for a network and an external storage device (not shown). Data such as a projection image obtained by the X-ray diagnostic apparatus 1, an analysis result, and the like can be transferred to another medical apparatus 35 via the interface unit and the network.

The dose graph generation unit 23 generates a dose graph indicating an area dose at the time of each of a plurality of X-ray irradiation operations and the sum of area doses (to be referred to as a total area dose hereinafter) from the start time of X-ray irradiation to the end time of each X-ray irradiation operation based on outputs from the dose measuring unit 135. The dose graph generation unit 23 calculates a total area dose by summing area doses from the start time of X-ray irradiation to the end time of each X-ray irradiation operation. That is, the dose graph generation unit 23 generates a dose graph indicating a plurality of area doses respectively corresponding to a plurality of imaging operations concerning X-ray irradiation based on dose information. In addition, the dose graph generation unit 23 sequentially updates a dose graph in accordance with the sequential acquisition of dose information.

More specifically, the dose graph generation unit 23 associates area doses with X-ray conditions. The dose graph generation unit 23 generates a dose graph indicating area doses respectively corresponding to a plurality of X-ray irradiation operations in the form of a bar graph, with the abscissa representing the number of times of imaging or the elapsed time (time series) from the start of imaging, and one ordinate representing the area doses, while indicating a total area dose from the start time of X-ray irradiation to the end time of each X-ray irradiation operation in the form of a line graph, with the other ordinate representing the total area doses. That is, the dose graph generation unit 23 generates a dose graph indicating area doses corresponding to imaging schemes (to be described later) along the time series of imaging.

Note that the dose graph generation unit 23 may generate a dose graph on which area doses corresponding to imaging schemes are plotted side by side for the respective imaging schemes. In addition, the dose graph generation unit 23 may sequentially update the display mode of displaying total area doses on a dose graph with an increase in area dose in imaging. The display mode indicating total area doses uses, for example, a polygonal line. Note that the dose graph generation unit 23 may generate a dose graph indicating area doses corresponding to imaging schemes so as to make the area dose identifiable for the respective X-ray irradiation regions of an object.

The dose graph generation unit 23 calculates a total area dose by adding area doses from the start time of X-ray irradiation to the end time of each X-ray irradiation operation. In addition, the dose graph generation unit 23 generates a bar graph of area doses with hues corresponding to X-ray imaging types (one-shot imaging and fluoroscopy) of X-ray conditions. A dose graph is generated as one dose graph throughout a period from the start of an examination to the end of the examination (to be referred to as an examination period hereinafter) in one examination of the same object P. Note that the dose graph generation unit 23 may generate a line graph indicating total area doses with a hue different from that of a bar graph indicating area doses. Note that the display mode setting unit 33 sets hues corresponding to X-ray imaging types and a hue indicating total area doses.

Note that the dose graph generation unit 23 may calculate a total area dose throughout a plurality of examinations when the plurality of examinations are executed on an object. In addition, at this time, the dose graph generation unit 23 can generate information indicating area doses and a total area dose as one dose graph in a total examination period throughout a plurality of examinations.

The dose graph generation unit 23 may generate a dose report concerning each of a plurality of X-ray imaging operations. A dose report is numerical information corresponding to a dose graph. The dose graph generation unit 23 outputs the generated dose graph and dose report to the output unit 29 and the storage unit 25.

A dose report has, for example, a plurality of pieces of dose information respectively corresponding to total imaging concerning a plurality of one-shot imaging operations and total fluoroscopy concerning a plurality of fluoroscopic operations of a plurality of X-ray imaging operations. Dose information concerning total imaging includes, for example, the sum of imaging times (to be referred to as a total imaging time hereinafter), the sum of imaging doses (to be referred to as a total imaging dose hereinafter), and the sum of area doses concerning a plurality of one-shot imaging operations (to be referred to as an imaging total area dose hereinafter). Dose information concerning total fluoroscopy includes, for example, the sum of fluoroscopy times (to be referred to as a total fluoroscopy time hereinafter), the sum of fluoroscopy doses (to be referred to as a total fluoroscopy dose hereinafter), and the sum of area doses concerning a plurality of fluoroscopic operations (to be referred to as a fluoroscopy total area dose hereinafter). In addition, a dose report may have a total dose and a total area dose throughout an examination period in a plurality of X-ray imaging operations.

More specifically, the dose graph generation unit 23 calculates an air kerma at a reference position based on the position of the support mechanism 13, a relative positional relationship (geometric conditions: for example, the imaging position of an object), an area dose, and an irradiation area. The dose graph generation unit 23 may generate a dose graph by using the doses (the patient skin doses, the area doses, and the like) calculated based on the calculated air kerma, X-ray conditions, an irradiation area, the position of the support mechanism 13, and a relative positional relationship (geometric conditions).

Note that the dose graph generation unit 23 may generate the detailed information of an area dose in each of a plurality of X-ray irradiation operations in accordance with an input to start each of X-ray irradiation operations. The detailed information of an area dose includes, for example, an imaging start time, imaging type, tube voltage, tube current, exposure time, pulse width, irradiation time, tube current-time product, air kerma, and X-ray irradiation region. The dose graph generation unit 23 outputs detailed information corresponding to an area dose to the output unit 29 and the storage unit 25.

The display mode setting unit 33 sets a display mode for a dose graph in accordance with each of a plurality of imaging schemes corresponding to imaging contained in dose information. An imaging scheme is defined by at least one of X-ray conditions corresponding to X-ray irradiation, an imaging type, a plurality of X-ray irradiation regions, and the imaging position of an object. A display mode includes a hue and shape corresponding to an imaging scheme in display of area doses on a dose graph. When an imaging scheme concerns one-shot imaging, a shape is equivalent to, for example, a rectangle corresponding to the magnitude of an area dose concerning this one-shot imaging on a dose graph. When an imaging scheme concerns fluoroscopy, a shape is equivalent to, for example, the extension of a rectangle corresponding to the magnitude of an area dose sequentially acquired in this fluoroscopy. That is, the display mode setting unit 33 sets a display mode of switching between display modes for area doses on a dose graph in accordance with an imaging scheme.

The storage unit 25 stores various types of projection images generated by the image generation unit 21, control programs for the X-ray diagnostic apparatus 1, a diagnosis protocol, the instruction issued by the operator and sent from the input unit 27, various types of data groups such as X-ray conditions, various types of data sent via the interface unit and a network, a total area dose, and the like. The storage unit 25 may also store the relative positional relationship between the X-ray tube 131 and the top 17.

The storage unit 25 stores the dose graph, dose information, detailed information, and dose report generated by the dose graph generation unit 23 together with a plurality of associated projection images. The storage unit 25 may also store a program concerning each processing executed by the dose graph generation unit 23. In addition, the storage unit 25 stores a plurality of pieces of hue information respectively corresponding to a plurality of X-ray imaging operations (one-shot imaging and fluoroscopic) under X-ray conditions. Note that the storage unit 25 may store a dose information generation program concerning each type of function, e.g., a function of generating a dose graph and a dose report, executed by the dose graph generation unit 23. Furthermore, the storage unit 25 may store a program (dose graph generation program) for executing dose graph generation processing.

The input unit 27 inputs X-ray conditions, fluoroscopy and imaging positions, an irradiation range, an X-ray irradiation region, and the like. More specifically, the input unit 27 inputs various types of instructions, commands, information, selections, and settings from the operator to the X-ray diagnostic apparatus 1. Fluoroscopy and imaging positions are defined by, for example, angles relative to the isocenter. The input unit 27 includes a foot switch which inputs instructions to start and end fluoroscopy. In addition, the input unit 27 includes a hand switch for the execution of one-shot imaging. The input unit 27 can also input display items to be displayed on a dose graph and a dose report. In addition, the input unit 27 can input units in display items on a dose graph and a dose report.

Although not shown, the input unit 27 includes a trackball, switch buttons, a mouse, and a keyboard which are used to make various types of settings. The input unit 27 detects the coordinates of the cursor displayed on a display screen, and outputs the detected coordinates to the control unit 31. Note that the input unit 27 may be touch panel provided so as to cover the display screen. In this case, the input unit 27 detects touched and designated coordinates by a coordinate reading principle such as an electromagnetic induction scheme, magnetostriction scheme, or a pressure-sensitive scheme, and outputs the detected coordinates to the control unit 31.

An output unit 29 outputs a dose graph accompanied by a set display mode. More specifically, the output unit 29 includes a monitor which displays dose graphs, projection images, and the like. The monitor sequentially updates and displays the above area dose corresponding to the imaging scheme on the dose graph along time series in accordance with the sequential acquisition of dose information. The monitor displays area doses corresponding to imaging schemes on a dose graph side by side for the respective imaging schemes. The output unit 29 outputs a dose graph to another medical apparatus 35 via a predetermined network. The monitor displays area doses corresponding to imaging schemes on a dose graph so as to make the area doses identifiable for the respective X-ray irradiation regions of the object. The monitor sequentially updates and displays a total area dose with an increase in area dose in imaging. For example, the monitor switches and displays area doses on a dose graph in accordance with a set display mode and an imaging scheme.

Figure 4:
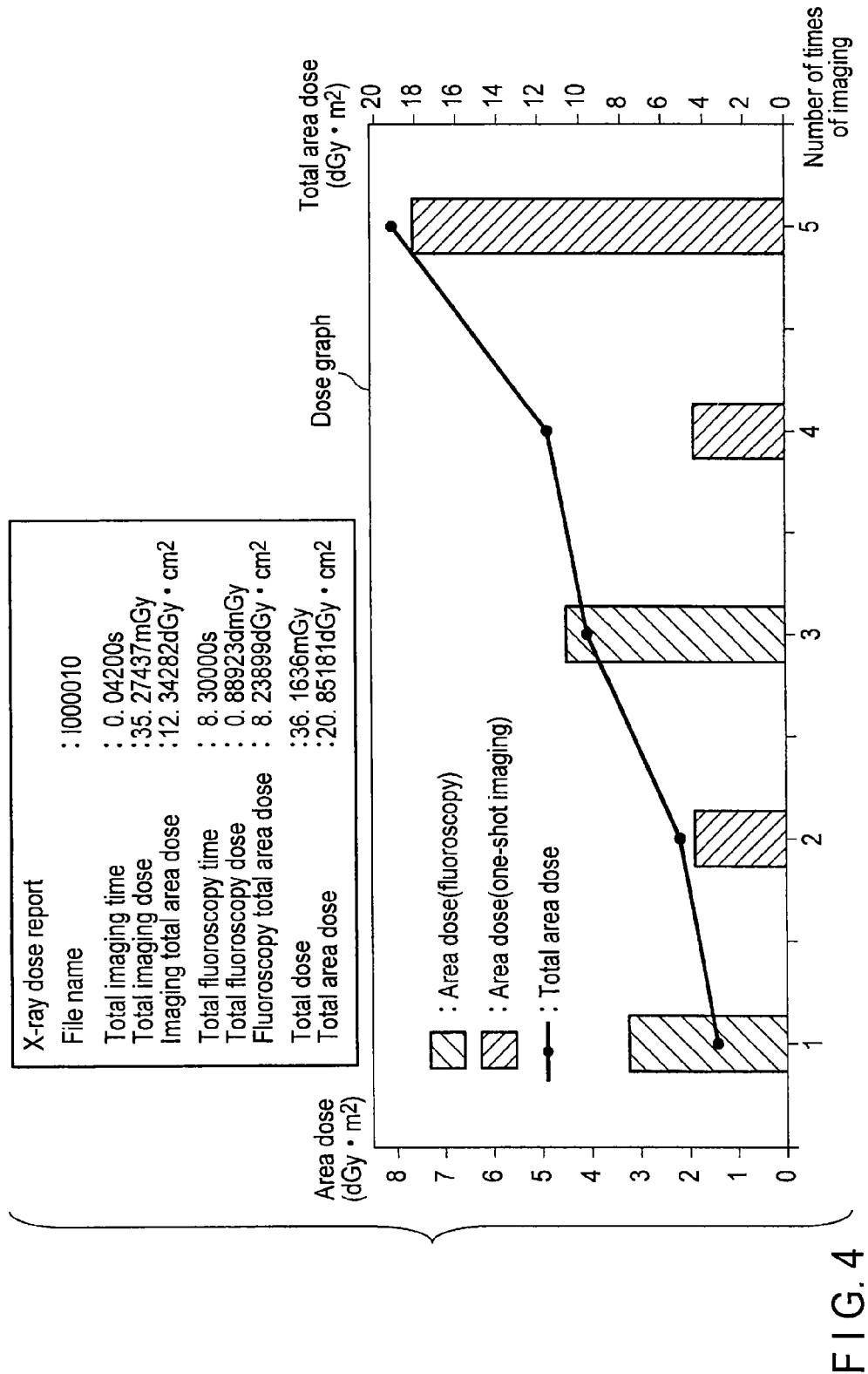
FIG. 4 is a view showing a display example of a dose graph together with a dose report according to this embodiment.

The monitor displays the projection image generated by the image generation unit 21. The monitor displays a dose graph together with a dose report. FIG. 4 is a view showing an example of displaying a dose graph together with a dose report. Referring to the dose graph shown in FIG. 4, the abscissa represents the number of times of imaging. Note that the abscissa of the dose graph may represent time. Referring to the dose graph shown in FIG. 4, the left ordinate represents area dose. On the dose graph, area doses corresponding to the number of times of imaging are indicated by vertical bars (bars). Referring to FIG. 4, each bar representing an area dose associated with fluoroscopy is indicated by oblique lines extending from the upper right to the lower left in a vertical bar like a histogram bar. Referring to FIG. 4, each bar representing an area dose associated with one-shot imaging is indicated by oblique lines extending from the upper left to the lower right in a vertical bar like a histogram bar.

Figure 12:
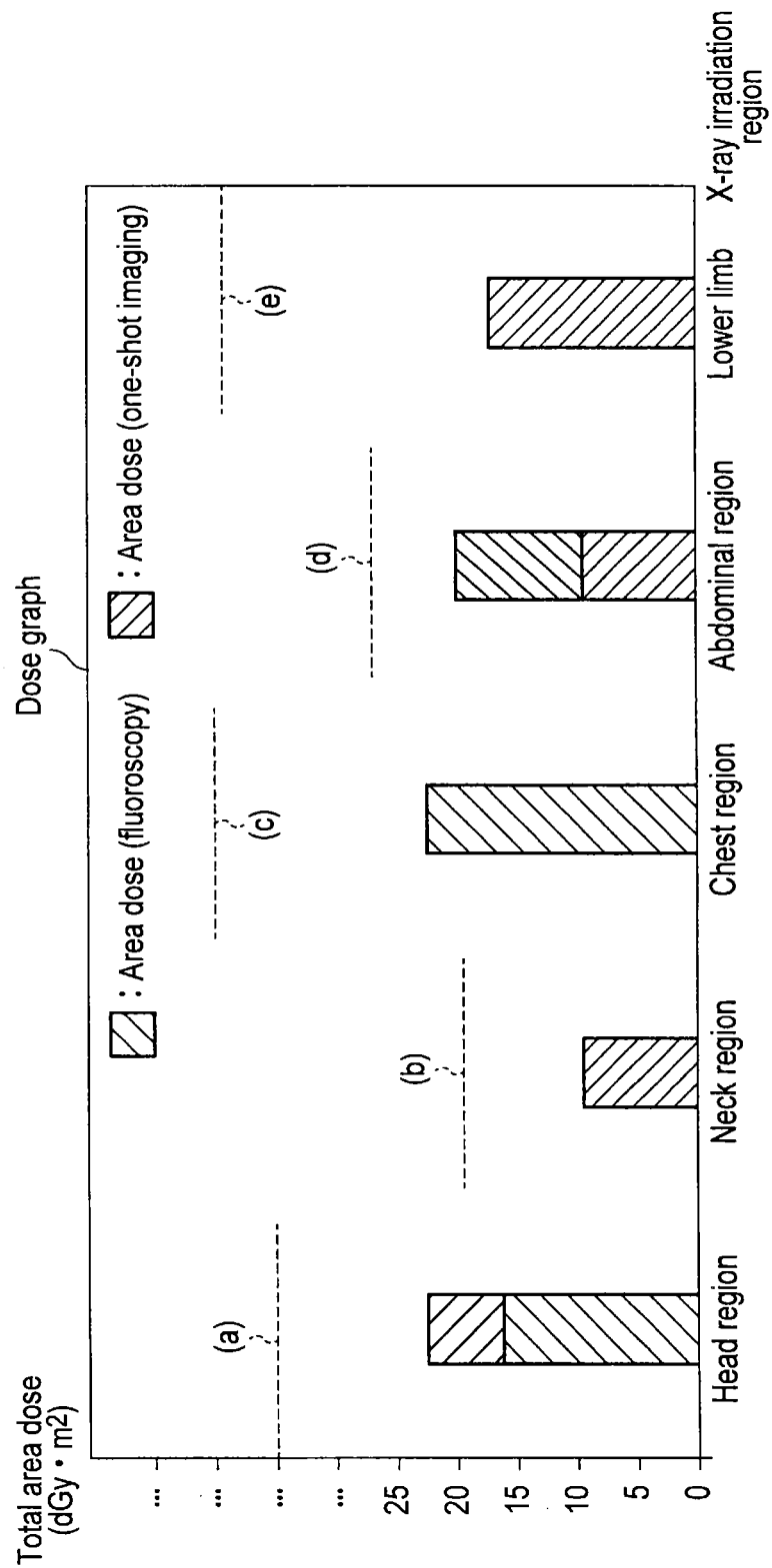
FIG. 12 is a view showing an example of identifiably displaying an area dose corresponding to an imaging scheme for each X-ray irradiation region of an object on a dose graph according to this embodiment.

FIG. 12 is a view showing an example of identifiably displaying an area dose corresponding to an imaging scheme for each X-ray irradiation region (discrete irradiation positions) of an object on a dose graph. FIG. 12 is a dose graph different from that in FIG. 4. The abscissa of the dose graph shown in FIG. 12 represents items of X-ray irradiation regions. The ordinate in FIG. 12 represents the total area dose at each X-ray irradiation region. In addition, the total area doses corresponding to the respective X-ray irradiation regions are discriminated according to the imaging schemes. Discrimination according to imaging schemes is performed by, for example, hues. The display mode setting unit 33 sets hues for discrimination according to imaging schemes.

Note that the monitor identifiably displays the area dose corresponding to the imaging scheme on the dose graph for at least one of each of a plurality of X-ray irradiation regions of the object and X-ray irradiation position of a height of the object. Then, the abscissa of the dose graph shown in FIG. 12 corresponds to continuous irradiation position of the height of the object.

Referring to FIG. 12, each bar indicating an area dose associated with fluoroscopy is indicated by oblique lines extending from the upper right to the lower left. Referring to FIG. 12, each bar indicating an area dose associated with one-shot imaging is indicated by oblique lines extending from the upper left to the lower right. Note that on a dose graph indicating total area doses corresponding to the items of X-ray irradiation regions, the upper limit value of a dose up to which X-ray irradiation is permitted (to be referred to as an upper dose limit value hereinafter) may be displayed for each X-ray irradiation region. A plurality of upper dose limit values respectively correspond to a plurality of X-ray irradiation regions.

A broken line (a) in FIG. 12 indicates an upper dose limit value when an X-ray irradiation region is a head region. A broken line (b) in FIG. 12 indicates an upper dose limit value when an X-ray irradiation region is a neck region. A broken line (c) in FIG. 12 indicates an upper dose limit value when an X-ray irradiation region is a chest region. A broken line (d) in FIG. 12 indicates an upper dose limit value when an X-ray irradiation region is an abdominal region. A broken line (e) in FIG. 12 indicates an upper dose limit value when an X-ray irradiation region is a lower limb.

When, for example, the operator performs a predetermined input operation via the input unit 27 while the dose graph shown in FIG. 4 is displayed, the dose graph shown in FIG. 4 is replaced with the dose graph shown in FIG. 12, and the dose graph shown in FIG. 12 is displayed. In this case, the predetermined input operation includes, for example, the operation of a switching button for dose graphs and the operation of selecting a dose graph to be displayed.

When a dose graph is displayed on the monitor, the vertical bars on the dose graph are displayed in different hues corresponding to imaging types. The display mode setting unit 33 sets hues for the bars on the dose graph in accordance with imaging schemes (e.g., imaging types). For example, each vertical bar representing an area dose associated with fluoroscopy is displayed in blue, and each vertical bar representing an area dose associated with one-shot imaging is displayed in yellow. Note that it is possible to change the hue of each vertical bar representing an area dose on the dose graph via the input unit 27, as needed. In addition, the monitor can display the display items input via the input unit 27 together with the dose graph. Furthermore, the monitor can display a dose graph and a dose report upon changing units in display items on the graph and report in accordance with the units input via the input unit 27.

Note that the monitor may always display a dose graph and a dose report during an examination period with respect to the object P. In addition, the monitor may pop-up display a dose graph and a dose report by a predetermined button operation via the input unit 27.

The control unit 31 includes a CPU (Central Processing Unit) and a memory (neither of which is shown). The control unit 31 temporarily stores, in the memory (not shown), information such as instructions, X-ray conditions including imaging conditions and fluoroscopy conditions which are sent from the input unit 27. The control unit 31 controls the respective units (e.g., the high voltage generation unit 11, the X-ray beam limiting unit 133, and the driving unit 19) of the X-ray diagnostic apparatus 1 to execute X-ray imaging (one-shot imaging and fluoroscopy) in accordance with operator instructions, fluoroscopy and imaging positions, X-ray conditions, and the like stored in the memory.

The control unit 31 reads out the dose information generation program stored in the storage unit 25 and loads the program in the memory. The control unit 31 controls the respective units (the dose measuring unit 135, the dose graph generation unit 23, the display mode setting unit 33, the output unit 29, and the like) of the X-ray diagnostic apparatus 1 in accordance with the dose information generation program loaded in the memory.

(Dose Graph Generation Function)

A dose graph generation function is a function of generating and displaying a dose graph based on the area dose acquired in each of a plurality of X-ray imaging operations. Processing associated with the dose graph generation function (to be referred to as dose graph generation processing hereinafter) will be described.

Figure 5:
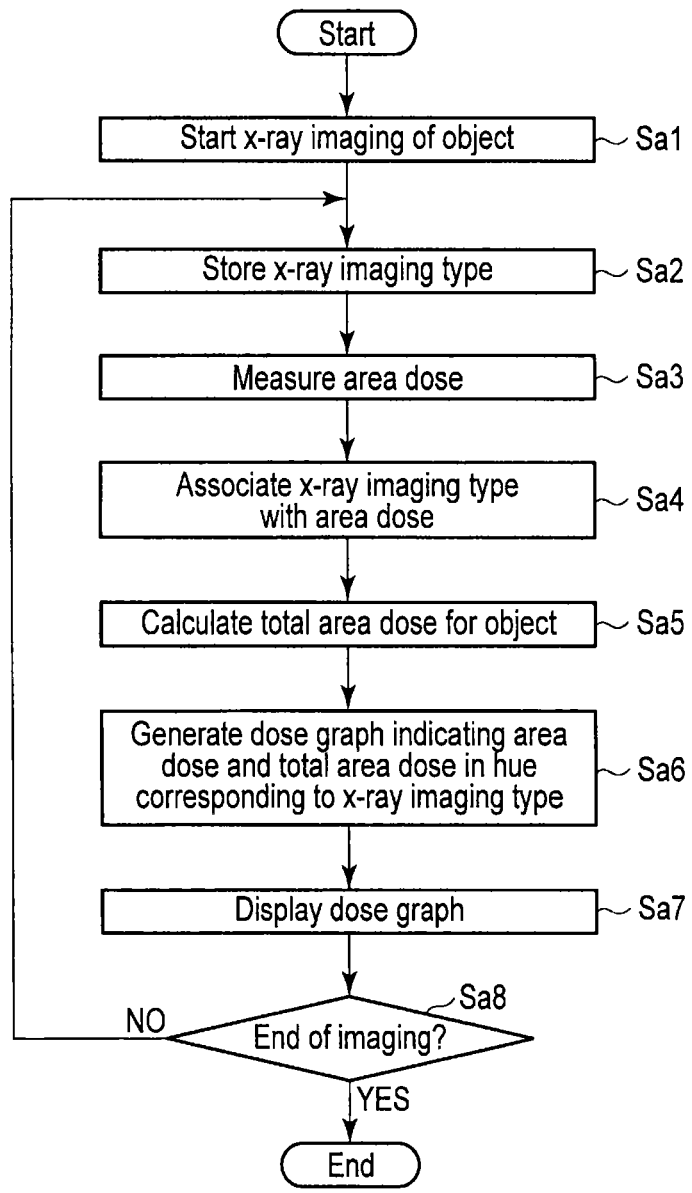
FIG. 5 is a flowchart showing an example of a procedure for dose graph generation processing according to this embodiment.

FIG. 5 is a flowchart showing an example of a procedure for dose graph generation processing.

X-ray imaging is started with respect to the object P (step Sa1). An X-ray imaging type (one-shot imaging or fluoroscopy) is stored in the storage unit 25 (step Sa2). An area dose is measured (step Sa3). The X-ray imaging type is associated with the area dose (step Sa4). A total area dose with respect to the object P is calculated (step Sa5). A dose graph is generated, which indicates the area dose and the total area dose with a hue corresponding to the X-ray imaging type (step Sa6).

The generated dose graph is displayed on the monitor (step Sa7). If X-ray imaging with respect to the object P is not complete, the processing in steps Sat to Sa7 is repeated (step Sa8).

First Modification

A difference from this embodiment is that when an area dose is selected on the dose graph displayed on the monitor via the input unit 27, detailed information concerning the selected area dose is displayed.

The input unit 27 inputs the designation of an area dose on the dose graph displayed on the monitor. More specifically, the input unit 27 moves the cursor on the vertical bar indicating the area dose in accordance with the instruction from the operator. When moving the cursor on the vertical bar, the input unit 27 specifies an area dose associated with the vertical bar on which the cursor is superimposed. A specified area dose will be referred to as a specific area dose hereinafter.

The input unit 27 becomes ready for a predetermined input operation while the cursor is superimposed on the vertical bar indicating the area dose. The predetermined input operation includes, for example, double clicking with the mouse and pressing a predetermined button. When a predetermined input operation (area dose designation instruction) is performed, the input unit 27 outputs, to the control unit 31, an instruction (to be referred to as a detailed information readout instruction hereinafter) to read out detailed information concerning a specific area dose from the storage unit 25.

Upon receiving the detailed information readout instruction from the input unit 27, the control unit 31 reads out detailed information concerning the specific area dose from the storage unit 25. The control unit 31 outputs the readout detailed information to the monitor of the output unit 29.

The monitor displays a cursor on a displayed dose graph. The monitor displays the detailed information read out from the control unit 31 together with a dose graph. The monitor displays X-ray conditions associated with X-ray irradiation corresponding to a designated area dose and the detailed information of the designated area dose together with the dose graph in response to the designation of the area dose via the input unit.

Figure 6:
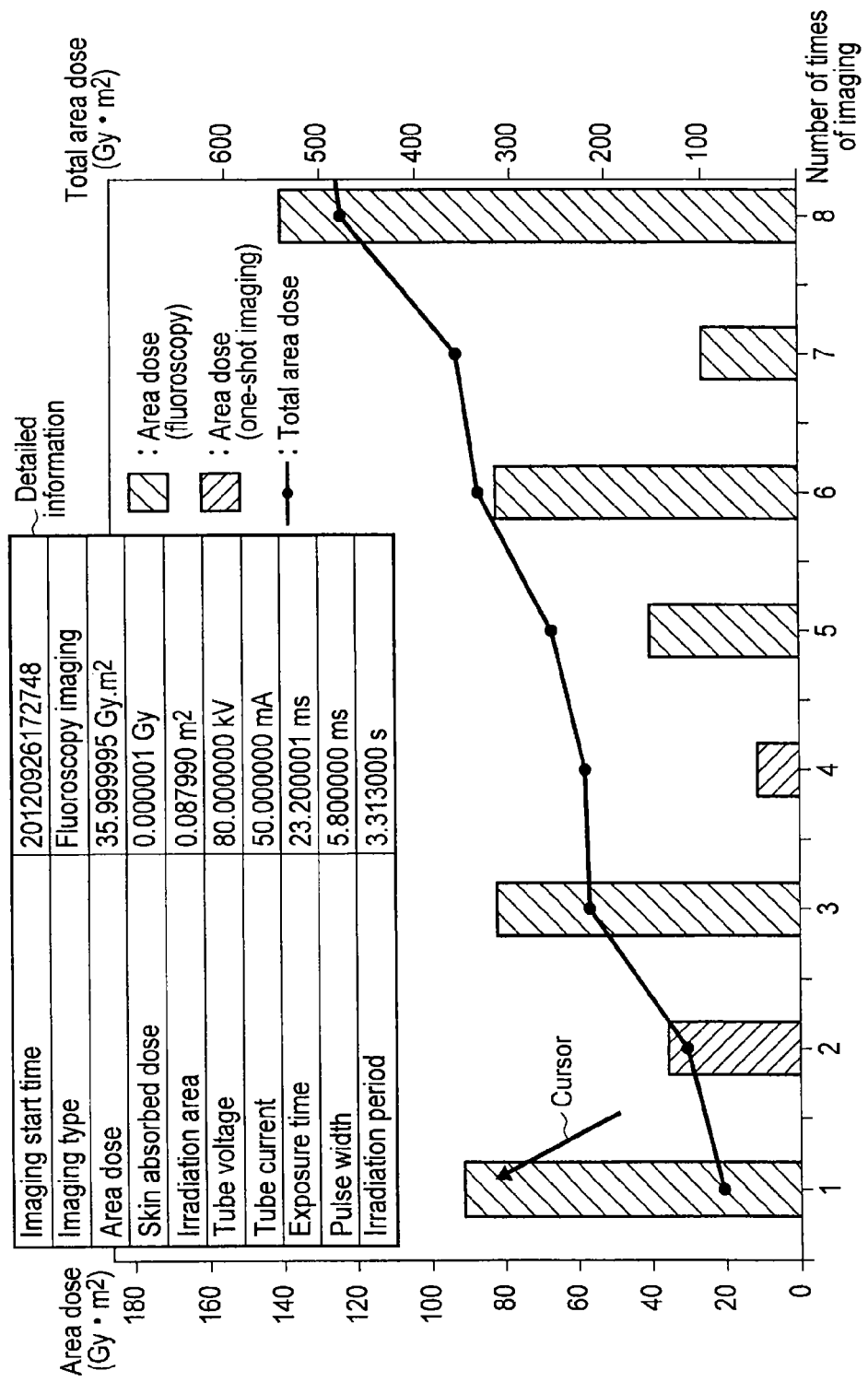
FIG. 6 is a view showing a display example of detailed information concerning a specific area dose together with a dose graph according to the first modification of this embodiment.

FIG. 6 is a view showing an example of displaying detailed information concerning a specific area dose together with a dose graph. As shown in FIG. 6, the specific area dose is an area dose in the first imaging operation. Referring to FIG. 6, the displayed detailed information is detailed information concerning the area dose in the first imaging operation. The detailed information shown in FIG. 6 includes an imaging start time, imaging type, area dose, skin absorbed dose, tube voltage, tube current, exposure time, pulse width, and irradiation time.

Note that the items presented as detailed information are not limited to the items of the detailed information in FIG. 6 (to be referred to as detailed information items hereinafter), and can be set as needed via the input unit 27. The number of detailed information items may be smaller than that of items shown in FIG. 6. In addition, detailed information items may include items such as a tube current-time product, air kerma, and imaging region. In addition, the input unit 27 can change the units in detailed information items as needed via the input unit 27. That is, detailed information items and units can be arbitrarily customized in accordance with an instruction from the operator via the input unit 27.

Second Modification

A difference from this embodiment is that a dose graph is dynamically updated and displayed during an execution period of X-ray imaging of the object P. For example, in an execution period of fluoroscopy, a bar indicating the area dose on the dose graph is dynamically extended and displayed.

Assume that, for the sake of a concrete description, each bar to be dynamically displayed indicates an area dose associated with fluoroscopy (moving image capturing).

The input unit 27 includes a button for selecting between fluoroscopy and one-shot imaging. When the operator presses a button for selecting fluoroscopy via the input unit 27, fluoroscopy is selected as X-ray imaging of the object P. The input unit 27 includes a switch (to be referred to as an irradiation switch hereinafter) to start irradiating the object P with X-rays. The input unit 27 outputs an instruction for executing X-ray irradiation with respect to the object P in accordance with X-ray conditions to the control unit 31 in accordance with the pressing of the irradiation switch.

When, for example, fluoroscopy is selected, the input unit 27 outputs an instruction to execute fluoroscopy to the control unit 31 over a period during which the irradiation switch is pressed. The input unit 27 outputs an input instruction corresponding to the pressing of the irradiation switch and an instruction to cancel the pressing of the irradiation switch to the dose measuring unit 135 and the dose graph generation unit 23. The instruction to cancel the pressing of the irradiation switch is equivalent to releasing the finger of the operator from the irradiation switch.

The control unit 31 executes X-ray imaging of the object P in accordance with the X-ray imaging type selected by the input unit 27 and the X-ray conditions. When, for example, fluoroscopy is selected as an X-ray imaging type via the input unit 27, the control unit 31 executes fluoroscopy over a period during which the irradiation switch is pressed.

The dose measuring unit 135 starts acquiring an area dose in response to an input instruction corresponding to the pressing of the irradiation switch. The dose measuring unit 135 continuously acquires area doses until an instruction to cancel the pressing of the irradiation switch. The dose measuring unit 135 outputs the continuously acquired area doses to the dose graph generation unit 23.

The dose graph generation unit 23 generates a dose graph on which vertical bars (bars) indicating area doses are changed dynamically (in real time) in accordance with the area doses continuously output in fluoroscopy. More specifically, the dose graph generation unit 23 displays a vertical bar indicating an area dose while extending the bar with an increase in area dose in, for example, fluoroscopy.

That is, the dose graph generation unit 23 sequentially updates the bar indicating the area dose on the dose graph in accordance with the sequential acquisition of area doses. The sequential updating operation of extending a bar indicating an area dose on a dose graph is executed by, for example, repeating steps Sa3, Sa4, and Sa6 in the flowchart of FIG. 5. Note that the dose graph generation unit 23 may sequentially update a polygonal line indicating the total area dose on the dose graph with an increase in area dose in imaging. The updating of the polygonal line between imaging operations is displayed as the updating of an inclination of the polygonal line. The sequential updating of a polygonal line indicating a total area dose is executed by repeating steps Sa3 to Sa6 in the flowchart of FIG. 5. If the first imaging operation is fluoroscopy, the updating of the polygonal line is displayed as the movement of the position of the start point of the polygonal line.

Note that when an instruction to cancel the pressing of the irradiation switch is input and a signal representing the pressing of the irradiation switch is input, the dose graph generation unit 23 generates a vertical bar indicating an area dose at a position corresponding to the next imaging operation on the dose graph.

The monitor displays a dose graph on which an area dose is updated in real time. The monitor displays an increase in area dose on the dose graph as the extension of a vertical bar (a change in shape). That is, the monitor displays the vertical bar indicating the area dose on the dose graph upon extending the bar in the ordinate direction. This displays an increase in area dose in fluoroscopy. The monitor displays the number of times of pressing the irradiation switch as the number of times of imaging by X-ray irradiation.

Figure 7:
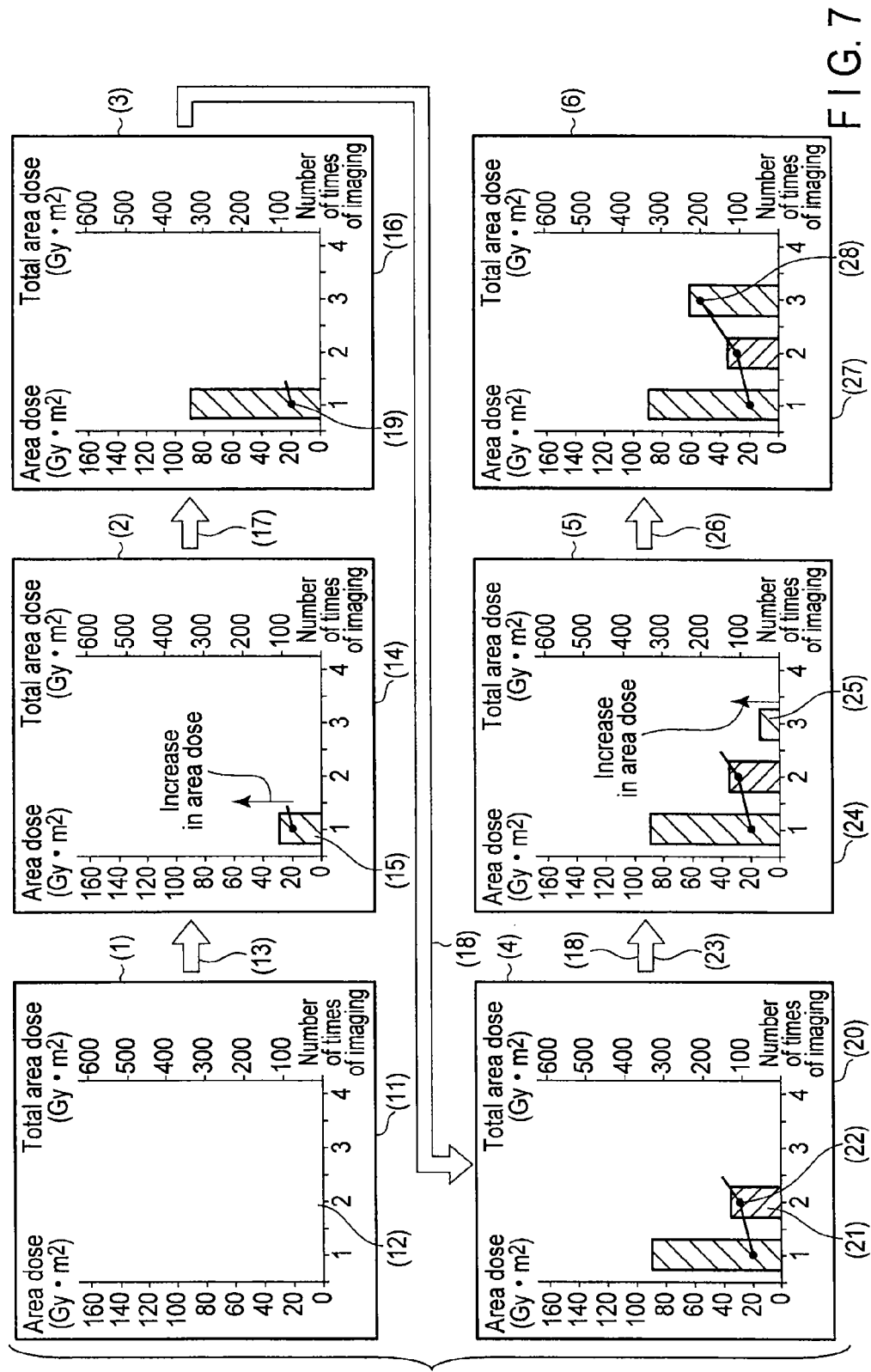
FIG. 7 is a view showing an example of dynamically increasing an area dose in each dose graph when three X-ray imaging operations are performed, with the first and third examination imaging operations being fluoroscopy and the second X-ray imaging being one-shot imaging, according to the second modification of this embodiment.

FIG. 7 is a view showing an example of dynamically extending a bar indicating an area dose on a dose graph when the first and third X-ray irradiation operations of three X-ray irradiation operations are fluoroscopy, and the second X-ray irradiation is one-shot imaging. (1) in FIG. 7 indicates a display screen (11) on which a dose graph (12) is displayed before the irradiation switch is turned on (13). (2) in FIG. 7 indicates an example of a dose graph during execution of the first imaging operation (fluoroscopy). (2) in FIG. 7 indicates the display screen (14) during the first imaging operation (fluoroscopy). That is, when the irradiation switch is turned on, a bar (15) indicating an area dose associated with the first imaging operation (fluoroscopy) is dynamically extended and displayed during fluoroscopy, as indicated by (2) in FIG. 7. At this time, the start point of a polygonal line indicating a total area dose may be moved upward along the ordinate of the graph with an increase in area dose.

(3) in FIG. 7 indicates a dose graph at the end of the first imaging operation. (3) in FIG. 7 indicates the display screen (16) at the end of the first imaging operation (fluoroscopy). That is, when the irradiation switch is turned off (17) in the first imaging operation, the monitor is set in a standby state to display a vertical bar indicating an area dose at the point corresponding to the next imaging operation, as indicated by (3) in FIG. 7. In other word, a bar indicating an area dose is transmitted to next column (the vertical bar) in the next imaging (18). A polygonal line (19) in (3) indicates a total area dose at the end of the first imaging operation (fluoroscopy). If the start point of the polygonal line indicating a total area dose is not moved with an increase in area dose, the start point is displayed on the dose graph together with the end of fluoroscopy.

(4) in FIG. 7 indicates a dose graph at the end time of the second imaging operation (one-shot imaging) when the irradiation switch is turned on. (4) in FIG. 7 indicates the display screen (20) at the end of the second imaging operation (one-shot imaging). That is, when the second imaging operation as one-shot imaging is executed, an area dose in the second imaging operation is additionally displayed as indicated by (4) in FIG. 7. A bar (21) in (4) indicates an area dose in the second imaging operation (one-shot imaging). The polygonal line (22) in (4) indicates the total area dose at the end of the second imaging operation (one-shot imaging).

(5) in FIG. 7 indicates an example of a dose graph during execution of the third imaging operation (fluoroscopy) when the irradiation switch is turned on (23) after the end of the second imaging operation. (5) in FIG. 7 indicates the display screen (24) during the third imaging operation (fluoroscopy). That is, when the irradiation switch is turned on (23), an area dose associated with the third imaging operation (fluoroscopy) is dynamically increased and displayed during fluoroscopy, as indicated by (5) in FIG. 7. A bar (25) in (5) indicates an area dose in the third imaging operation (fluoroscopy). At this time, an inclination of a polygonal line indicating a total area dose between the second and third imaging operations may be displayed on the dose graph with an increase in area dose in the third imaging operation.

(6) in FIG. 7 indicates a dose graph at the end time of the third imaging operation. The end time of the third image operation is when the irradiation switch is turned off (26). (6) in FIG. 7 indicates the display screen (27) at the end of the third imaging operation (fluoroscopy). The polygonal line (28) in (6) indicates the total area dose at the first to the third imaging operations. As indicated by (2) to (6) in FIG. 7, a total area dose is displayed as a line graph every time X-ray imaging of the object P is terminated.

Third Modification

A difference from this embodiment is that a predetermined threshold set in advance for a total area dose is superimposed and displayed on a dose graph, and when a total area dose exceeds the predetermined threshold, the last area dose contributing to the exceedance of the predetermined threshold is displayed upon being changed to a predetermined hue.

The storage unit 25 stores the predetermined threshold for a total area dose. Note that the input unit 27 can change the predetermined threshold, as needed, in accordance with an instruction from the operator via the input unit 27. The predetermined threshold corresponds to, for example, the maximum allowable value of the X-ray radiation doses of a total area dose set in advance for the object P. The storage unit 25 outputs the predetermined threshold to the dose graph generation unit 23.

The dose graph generation unit 23 superimposes and displays the predetermined threshold read out from the storage unit 25 on the dose graph. The dose graph generation unit 23 may associate the predetermined threshold with a specific hue. The specific hue is a hue which can be easily identified by the operator. The specific hue is, for example, red.

The display mode setting unit 33 sets a specific hue corresponding to the display of a predetermined threshold. When a total area dose exceeds the predetermined threshold, the display mode setting unit 33 performs setting to change the hue of a bar indicating an area dose corresponding to an imaging scheme contributing to the exceedance of the threshold into a predetermined hue on the dose graph.

The monitor superimposes and displays the predetermined threshold on the dose graph. When the total area dose exceeds the predetermined threshold, the monitor displays the last area dose contributing to the exceedance of the predetermined threshold upon changing the hue of the dose to a predetermined hue. The predetermined hue is a hue which can be easily identified by the operator. The predetermined hue is, for example, orange. Note that when a total area dose exceeds a predetermined threshold, a predetermined notification (e.g., warning) may be displayed. Note that the output unit 29 may output a predetermined warning sound when a total area dose exceeds a predetermined threshold.

The monitor may display the area doses on the dose graph in FIG. 4 upon changing the display mode of the area doses in accordance with the ratio of the total area dose to a predetermined threshold. More specifically, the monitor displays a bar indicating an area dose which is sequentially updated on a dose graph while changing the hue of the bar in accordance with the ratio. Note that the monitor may superimpose and display the ratio on the dose graph. In addition, the monitor may display the difference value obtained by subtracting the ratio from 1 as the ratio of the remaining dose (to be referred to as the irradiation enable remaining dose hereinafter) based on the dose up to which X-ray irradiation is permitted. The monitor can also display a total area dose for each X-ray irradiation region on the dose graph in FIG. 12 upon changing the display mode of each total area dose in accordance with the ratio of the total area dose for each X-ray irradiation region to the upper dose limit value. Furthermore, the monitor may display the ratio of the total area dose for each X-ray irradiation region to the upper dose limit value.

For example, the dose graph generation unit 23, the control unit 31, and the like calculate the ratio of a total area dose to a predetermined threshold and the ratio of a total area dose for each X-ray irradiation region to the upper dose limit value. Note that the dose graph generation unit 23 may calculate a ratio based on the inclination of a polygonal line between imaging operations.

The display mode setting unit 33 sets a hue into which a hue change is made in accordance with a ratio. If, for example, the ratio is equal to or more than 70% or less than 80%, the display mode setting unit 33 sets the hue of a bar to yellow. If, the ratio is equal to or more than 80% or less than 90%, the display mode setting unit 33 sets the hue of a bar to orange. If for example, the ratio is equal to or more than 90% or less than 100%, the display mode setting unit 33 sets the hue of a bar to red. When the ratio exceeds a predetermined value, the output unit 29 may output a predetermined warning. The predetermined value is, for example, 95%.

FIG. 8 is a view showing a predetermined threshold together with a dose graph. As shown in FIG. 8, the predetermined threshold is displayed, parallel to the abscissa of the dose graph, in a predetermined hue (the long broken line in FIG. 8). In addition, as shown in FIG. 8, when a total area dose exceeds the predetermined threshold, the last area dose contributing to the exceedance of the predetermined threshold is displayed in a predetermined hue (the cross hatching in FIG. 8).

Fourth Modification

A difference from this embodiment is that a dose graph is stored in a predetermined storage form.

The storage unit 25 stores a generated dose graph in a predetermined storage form together with a plurality of projection images associated with the dose graph and information concerning a dynamic change in area dose on the dose graph. The predetermined storage form is, for example, Dose SR form in DICOM (Digital Imaging and COmmunications in Medicine). This makes it possible for another medical image display device to display a dose graph together with dynamic updating of an area dose, as needed, even after the end of an examination.

The storage unit 25 stores a dose graph together with a single projection image or a plurality of associated projection images in a storage medium such as an optical medium in a predetermined storage form. A storage medium is, for example, a CD-R, flash memory, HDD, or the like. Note that the storage unit 25 can also output a dose graph together with a single projection image or a plurality of associated projection images to an external medical image archiving apparatus or the like via an interface unit and a network. At this time, the storage unit 25 outputs a dose graph to a storage medium in a form included in DICOM DIR. The dose graph stored in the storage medium is displayed on a medical image display device, PC, and the like.

Figure 9:
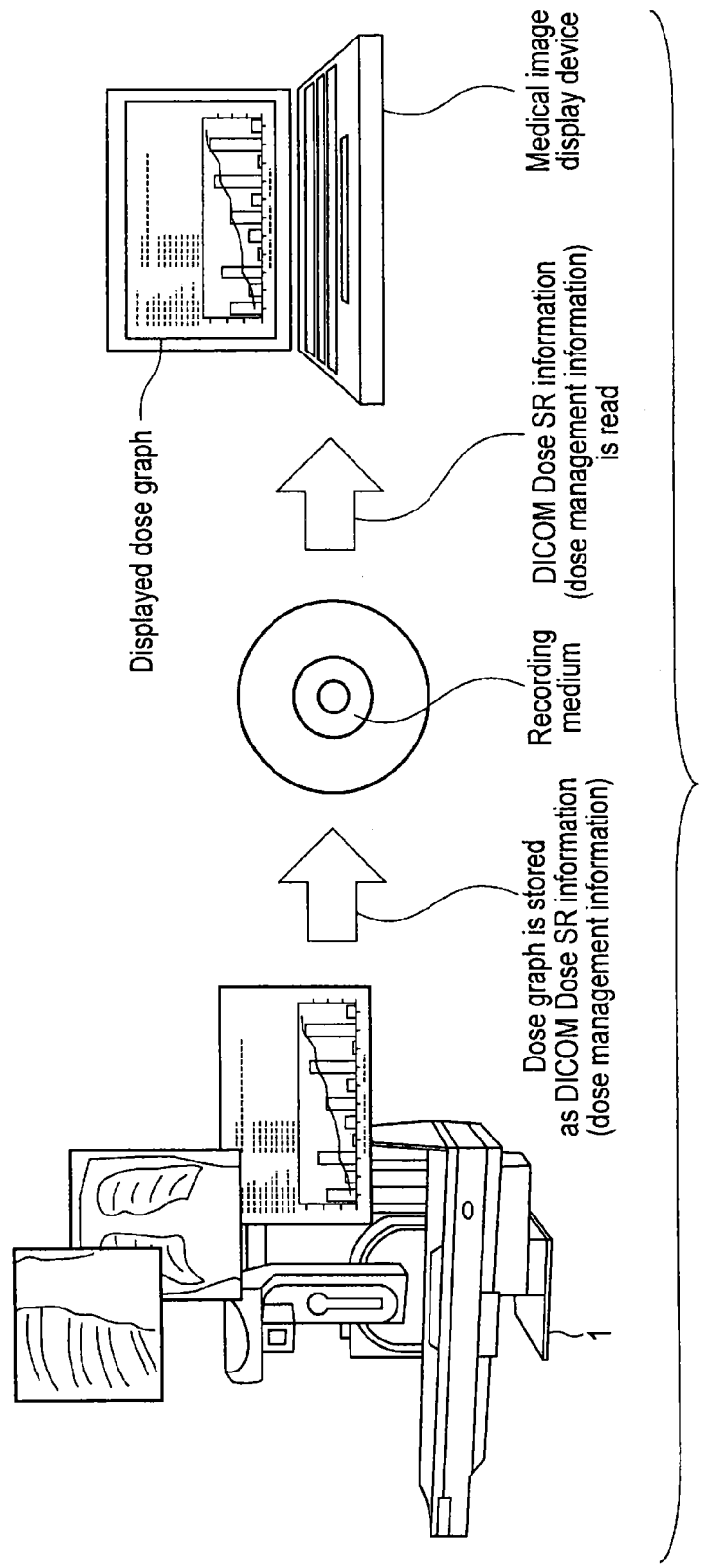
FIG. 9 is a view showing an example of a dose graph displayed on a medial image display device by storing the dose graph as dose management information such as DICOM Dose SR information in a storage medium and reading the information from the storage medium according to the fourth modification of this embodiment.

FIG. 9 is a view showing an example of a dose graph displayed on the medical image display device by storing the dose graph as dose management information such as DICOM Dose SR information in the storage medium and reading the DICOM Dose SR information from the storage medium. As shown in FIG. 9, storing DICOM Dose SR information in the storage medium in a form included in DICOM DIR makes it possible to display a dose graph on an arbitrary medical image display device included in a PC (Personal Computer).

Fifth Modification

A difference from this embodiment is that an area dose is acquired by calculating it based on X-ray conditions in each of a plurality of X-ray imaging operations.

Figure 10:
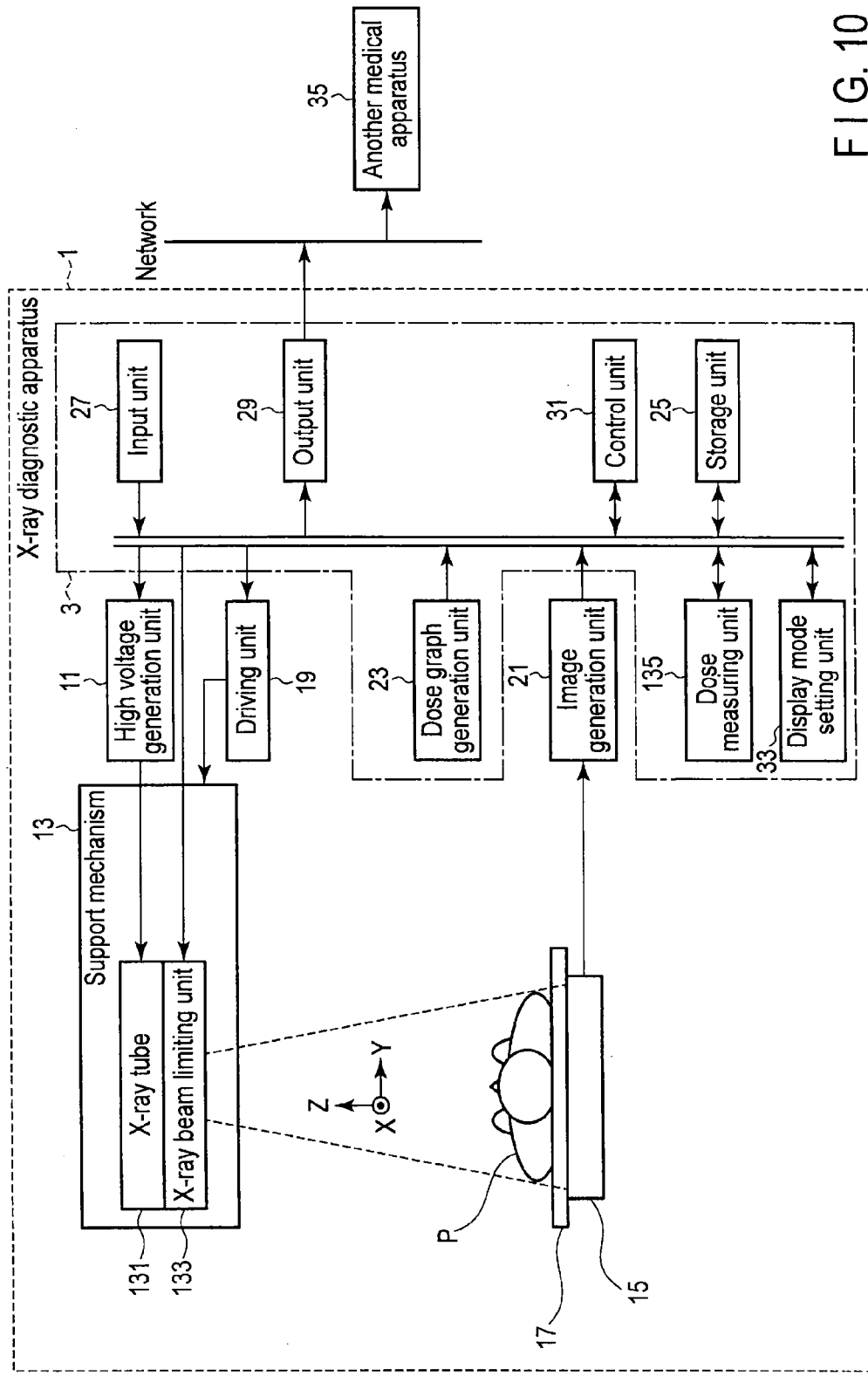
FIG. 10 is a block diagram showing the arrangement of an X-ray diagnostic apparatus according to the fifth modification of this embodiment.

FIG. 10 is a block diagram showing the arrangement of the X-ray diagnostic apparatus 1 according to this modification.

As shown in FIG. 10, the dose measuring unit 135 is not equipped with the support mechanism 13 unlike the arrangement shown in FIG. 1. The dose measuring unit 135 calculates an area dose based on X-ray conditions in each of a plurality of X-ray imaging operations. More specifically, the dose measuring unit 135 calculates an area dose in each X-ray imaging operation based on the tube voltage, tube current-time product, SID, irradiation range, and predetermined constant in the X-ray conditions. The dose measuring unit 135 outputs the calculated area dose to the dose graph generation unit 23 and the storage unit 25.

Note that the dose measuring unit 135 calculates an air kerma at a reference position based on the position of the support mechanism 13, a relative positional relationship (geometric condition), an area dose, and an irradiation area. The dose measuring unit 135 calculates a dose (patient skin dose) based on the calculated air kerma, imaging conditions, irradiation area, and position of the support mechanism 13, and relative positional relationship (geometric condition).

According to the above arrangement, the following effects can be obtained.

The X-ray diagnostic apparatus 1 according to this embodiment can display dose information over an examination period from the start of the examination to the end of the examination upon graphing the information. More specifically, the X-ray diagnostic apparatus 1 can generate and display a dose graph indicating an area dose and a total area dose in each of a plurality of X-ray irradiation operations in an examination period. An area dose is displayed as, for example, a bar graph on a dose graph. A total area dose is displayed as a line graph on a dose graph. That is, according to the X-ray diagnostic apparatus 1, there is provided an X-ray diagnostic apparatus which can display the transition state of dose information in a plurality of X-ray irradiation operations. The X-ray diagnostic apparatus 1 allows the operator to more easily grasp the transition of the exposure dose for the object P accompanying each of a plurality of X-ray imaging operations.

In addition, according to this embodiment, it is possible to identifiably display an area dose corresponding to an imaging scheme for each X-ray irradiation region of an object in the form of a dose graph. This allows the operator to easily grasp a total area dose for each X-ray irradiation region.

According to the first modification of this embodiment, detailed information concerning a specific area dose on a dose graph can be displayed in accordance with a predetermined operation by the input unit 27. This makes it possible for the operator to more easily grasp the detailed information of the exposure dose for the object P accompanying each of a plurality of X-ray irradiation operations. As described above, the X-ray diagnostic apparatus 1 can present detailed information concerning the object P to the operator by displaying the detailed information of an area dose for the object P in accordance with a predetermined operation.

According to the second modification of this embodiment, a dose graph is dynamically updated and displayed during an execution period of X-ray imaging of the object P. That is, the X-ray diagnostic apparatus 1 can display area doses and a total area dose on a dose graph dynamically (in real time) during an execution period of fluoroscopy. With this operation, the X-ray diagnostic apparatus 1 can present a dose for the object P to the operator by displaying the transition of the dose for the object P and an x-ray imaging type during an examination.

According to the third modification of this embodiment, it is possible to superimpose and display a predetermined threshold set in advance for total area doses on a dose graph and display the last area dose contributing to the exceedance of a predetermined threshold when a total area dose has exceeded the predetermined threshold upon changing the hue of the area dose into a predetermined hue. In addition, according to the X-ray diagnostic apparatus 1, it is possible to display the last area dose contributing to the exceedance of the predetermined threshold in a predetermined hue. As described above, the X-ray diagnostic apparatus 1 allows the operator to easily grasp a reference for a radiation dose permitted for the object P with respect to a default value of a total radiation dose.

In addition, according to this embodiment, it is possible to display a dose graph while changing the hue of each bar indicating an area dose sequentially updated on the dose graph in accordance with the ratio of a total area dose to a maximum allowable value, and to superimpose and display the ratio on the dose graph. According to this embodiment, it is possible to display the difference value obtained by subtracting the above ratio from 1 as the ratio of an irradiation enable dose. In addition, according to the embodiment, it is possible to display the total area dose for each X-ray irradiation region on a dose graph upon changing the display mode of the total area dose in accordance with the ratio of the total area dose for each X-ray irradiation region to the upper dose limit value, and to display the ratio of the total area dose for each X-ray irradiation region to the upper dose limit value. As described above, according to this embodiment, it is possible to easily grasp the ratio of a total area dose to the maximum allowable value or the upper dose limit value or an irradiation enable dose. That is, according to the embodiment, it is possible to display the above ratio and difference value as a guide reference for an imaging scheme and imaging time associated with X-ray imaging with reference to a maximum allowable value/upper dose limit value. This makes it possible to improve the safety of exposure for an object.

According to the fourth modification of this embodiment, it is possible to store a dose graph together with information concerning a dynamic change in area dose on the dose graph in an arbitrary storage medium in a predetermined storage form. For example, a dose graph can be displayed on an arbitrary medical image display device together with dynamic updating of an area dose after the end of an examination. This allows the operator to display a dose graph on a medical image display device including a PC without limitation to the X-ray diagnostic apparatus 1.

According to the fifth modification of this embodiment, it is possible to acquire an area dose by calculating an area dose based on X-ray conditions in each of a plurality of X-ray imaging operations. This makes it possible for even an X-ray diagnostic apparatus including no dosimeter to generate a dose graph.

As has been described above, the X-ray diagnostic apparatus 1 can present a dose for the object P to the operator by displaying the transition of the dose for the object P and an X-ray imaging type. This can effectively make the operator conscious of the attempt to reduce excessive exposure of the object P to X-rays.

In addition, the functions associated with this embodiment and the modifications can also be implemented by installing a program (dose graph generation program) for the execution of dose graph generation processing in the computer of the X-ray diagnostic apparatus 1 and expanding the program in the memory. In this case, the program which can cause the computer to execute this method can be distributed upon being stored in a recording medium such as a magnetic disk (a Floppy® disk, hard disk, or the like), an optical disk (a CD-ROM, DVD, or the like), or a semiconductor memory.

Figure 11:
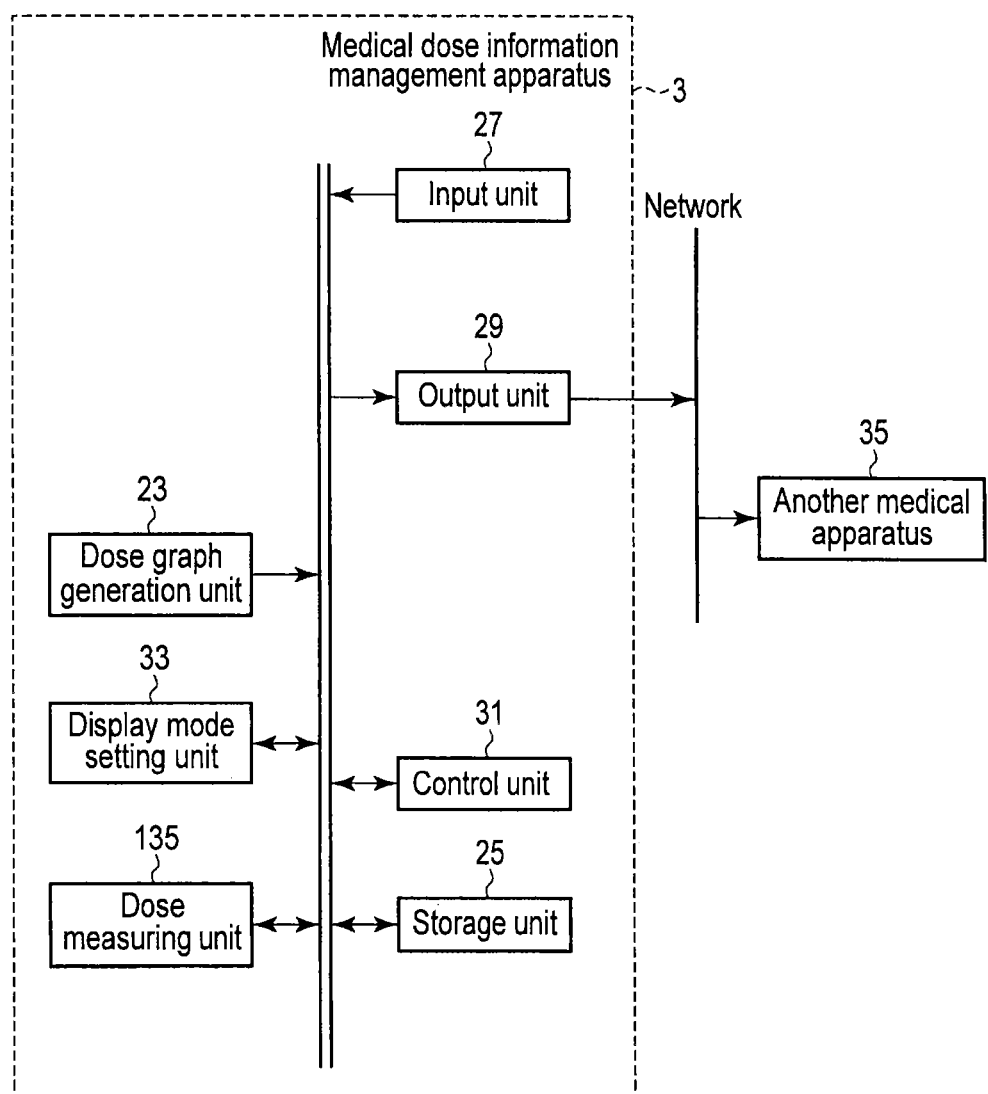
FIG. 11 is a block diagram showing an example of the arrangement of a medical dose information management apparatus according to this embodiment.

In addition, when the technical idea of the X-ray diagnostic apparatus 1 is to be implemented by a medical dose information management apparatus 3 as a modification of the above embodiment, for example, the apparatus includes the constituent elements shown in FIG. 11. The respective units in FIG. 11 have the same functions as those of the respective units having the same terms as those shown in FIGS. 1 and 10. When the X-ray diagnostic apparatus 1 is equipped with the medical dose information management apparatus 3, for example, the constituent elements enclosed by the one-dot dashed line in FIG. 10 correspond to those of the medical dose information management apparatus 3. Each processing by the dose graph generation function and the like in the medical dose information management apparatus 3 is executed in the same manner as in the above embodiment and each modification.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical dose information management apparatus comprising:
processing circuitry configured to
acquire dose information including an area dose in X-ray irradiation;
generate, based on the dose information, a dose graph indicating a plurality of area doses respectively corresponding to a plurality of imaging operations associated with the X-ray irradiation;
set a display mode for the dose graph in accordance with each of a plurality of imaging schemes corresponding to the imaging operations included in the dose information; and
output the dose graph accompanied by the set display mode.

2. The apparatus according to claim 1, wherein the processing circuitry is configured to
sequentially acquire the dose information in accordance with the imaging operations, and
sequentially update the dose graph in accordance with sequential acquisition of the dose information.

3. The apparatus according to claim 1, further comprising a monitor configured to display the dose graph.

4. The apparatus according to claim 3, wherein the monitor is configured to display the area dose corresponding to the imaging scheme on the dose graph along time series.

5. The apparatus according to claim 3, wherein the monitor is configured to display the area doses corresponding to the imaging schemes on the dose graph for the respective imaging schemes side by side.

6. The apparatus according to claim 1, wherein the processing circuitry is configured to output the dose graph to another medical apparatus via a predetermined network.

7. The apparatus according to claim 3, further comprising an input circuitry configured to designate at least one area dose of the area doses on the dose graph,
wherein the monitor is configured to display, together with the dose graph, an X-ray condition associated with the X-ray irradiation corresponding to the designated area dose and detailed information of the designated area dose in response to designation of the area dose.

8. The apparatus according to claim 1, wherein the imaging scheme is defined by at least one of an X-ray condition corresponding to the X-ray irradiation, a type of the imaging, a plurality of X-ray irradiation regions of an object, and an imaging position of the object, and
the display mode is configured to utilize a hue and a shape which correspond to the imaging scheme when displaying the area dose on the dose graph.

9. The apparatus according to claim 3, wherein the monitor is configured to identifiably display the area dose corresponding to the imaging scheme on the dose graph for at least one of each of a plurality of X-ray irradiation regions of an object and X-ray irradiation position of a height of the object.

10. The apparatus according to claim 3, wherein on the dose graph, the monitor is configured to display, with changing a hue of a bar into a predetermined hue, the bar indicating the area dose corresponding to the imaging scheme which contributes to excess of a threshold when a total area dose obtained by summing the area doses exceeds a predetermined threshold.

11. The apparatus according to claim 10, wherein the monitor is configured to superimpose the predetermined threshold on the dose graph and display the predetermined threshold in a specific hue.

12. The apparatus according to claim 10, wherein the monitor is configured to sequentially update the total area dose with an increase in the area dose in each of the imaging operations.

13. The apparatus according to claim 10, wherein the monitor is configured to display the area dose on the dose graph with changing the display mode of the area dose in accordance with a ratio of the total area dose to the predetermined threshold.

14. The apparatus according to claim 13, wherein the monitor is configured to display, with changing the hue of the bar in accordance with the ratio, the bar indicating the area dose updated sequentially on the dose graph.

15. The apparatus according to claim 13, wherein the processing circuitry is configured to output a predetermined notification when the ratio exceeds the threshold.

16. An X-ray diagnostic apparatus comprising:
an X-ray tube configured to generate X-rays;
a dosimeter configured to acquire dose information including a plurality of area doses respectively corresponding to a plurality of imaging operations in X-ray irradiation by the X-ray tube;
processing circuitry configured to
generate a dose graph indicating the area dose based on the dose information; and
set a display mode for the dose graph in accordance with a plurality of imaging schemes corresponding to the imaging operations included in the dose information; and
a monitor configured to display the dose graph accompanied by the set display mode.

17. A medical dose information management method comprising:
sequentially acquiring dose information including an area dose in X-ray irradiation in accordance with each of a plurality of imaging operations;
generating, based on the dose information, a dose graph indicating a plurality of area doses respectively corresponding to the imaging operations associated with the X-ray irradiation along time series in the imaging operations;
setting a display mode for the dose graph in accordance with each of a plurality of imaging schemes corresponding to the imaging operations included in the dose information;
sequentially updating the dose graph in accordance with sequential acquisition of the dose information; and
displaying the sequentially updated dose graph in the display mode.

* * * * *

UNITED STATES PATENT AND TRADEMARK OFFICE
CERTIFICATE OF CORRECTION

PATENT NO. : 9,566,036 B2
APPLICATION NO. : 14/446646
DATED : February 14, 2017
INVENTOR(S) : Takahiro Kuroki et al.

It is certified that error appears in the above-identified patent and that said Letters Patent is hereby corrected as shown below:

On the Title Page

Item (30), the Foreign Application Priority Data has been omitted. Item (30) should read:
(30) Foreign Application Priority Data
July 30, 2013 (JP)......................2013-157978

Signed and Sealed this
Sixth Day of March, 2018

Andrei Iancu
*Director of the United States Patent and Trademark Office*